(12) United States Patent
Vetter et al.

(10) Patent No.: US 6,223,408 B1
(45) Date of Patent: May 1, 2001

(54) APPARATUS FOR PLACING OBJECT IN SYRINGE BODY

(75) Inventors: Udo J. Vetter, Ravensburg; Klaus Steinbach; Anton Hecht, both of Baienfurt, all of (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 0 days.

(21) Appl. No.: 09/624,479

(22) Filed: Jul. 24, 2000

(30) Foreign Application Priority Data

Jul. 29, 1999 (DE) .............................. 199 35 681

(51) Int. Cl.⁷ .................................................. B23P 19/04
(52) U.S. Cl. ................................. 29/235; 29/234; 29/278
(58) Field of Search .......................... 29/235, 234, 278, 29/238, 239

(56) References Cited

U.S. PATENT DOCUMENTS

| | | | |
|---|---|---|---|
| 4,141,129 | * | 2/1979 | Martini .................................. 29/235 |
| 6,012,209 | * | 1/2000 | Whetstone ............................. 29/235 |
| 6,108,884 | * | 8/2000 | Casteman et al. ..................... 29/235 |

* cited by examiner

Primary Examiner—Stephen F. Gerrity
Assistant Examiner—Lee Wilson
(74) Attorney, Agent, or Firm—Herbert Dubno Andrew Wilford

(57) ABSTRACT

An object, e.g. a piston or a fluid medicament, is inserted into a tubular syringe body centered on a syringe axis and having a pair of ends by an apparatus having a support movable axially forward toward and axially rearward away from the body and a tube extending along a sleeve axis generally parallel to the syringe axis, having a rear end fixed in the support and a front end fittable inside the syringe. A centering sleeve is formed centered on the sleeve axis with a generally frustoconical centering surface engageable with the rear body end surrounding the tube. This sleeve is displaceable axially on the support between a front position with the centering surface projecting axially forward past the tube front end and a rear position with the tube front end projecting axially forward past the centering surface. The support is displaced axially forward toward the body and thereby engages the centering surface coaxially with the body rear end. Thereafter the tube is pressed coaxially through the centering sleeve into the syringe body and the object is expelled from its front end.

9 Claims, 6 Drawing Sheets

APPARATUS FOR PLACING OBJECT IN SYRINGE BODY

FIELD OF THE INVENTION

The present invention relates to an apparatus for placing an object in a syringe body. More particularly this invention concerns an apparatus for setting a partition piston or for filling a fluid into a syringe body.

BACKGROUND OF THE INVENTION

A standard prefilled hypodermic syringe comprises a tubular glass syringe body having a restricted front end that is provided with tip cap or needle. Around midway of its length the body is formed with a bypass passage constituted as a radially inwardly open and axially extending bypass groove. The interior of the syringe is subdivided by a front partition piston set just rearward of the bypass groove into a front compartment defined between the front partition piston and the front body end and a rear compartment bounded rearward by a rear piston fixed to a plunger that extends out a rear end of the body. A medicament, which may be a lyophilized powder or a liquid, is held in the front compartment and a solvent, typically water, is held in the rear compartment. For use the rear plunger is pressed forward so as to shift the front piston forward until it is level with the bypass passage which therefore opens into both the front and rear compartments, at which time the front piston stops moving while the liquid is forced by the rear piston through the bypass passage into the front compartment where it can mix with the medicament therein. Once the rear compartment is empty, the rear piston abuts the rear face of the front piston and the two move forward together to express the solution through the needle from the front compartment. The system can also be used with a medicament having two components that need to be mixed immediately before use.

Thus to make such a syringe it is necessary first to accurately set the front piston in place, then fill the rear compartment and set the rear piston and plunger in place, invert the assembly, and fill the medicament into the front compartment and install a tip cap or needle. Both of these operations—setting the rear piston in place and filling fluids into the compartments—are done by an apparatus which inserts a tube into the syringe body.

More particularly the front piston is set in place by compressing and fitting it into the front end of a setting tube whose outside diameter is slightly less than the inside diameter of the syringe body. This tube, with the piston fitted to its end, is inserted into the rear end of the piston until it is just rearward of where the piston should be set, then the piston is pressed forward out of the setting tube, whereupon its natural elasticity causes it to expand radially and set itself stably in place in the syringe body. Then the setting tube is withdrawn rearward.

To fill the fluid medicament or solid into one of the compartments, the syringe body is oriented with the compartment to be filled open upward and the filling apparatus inserts a filling tube down into the syringe. Once this tube is near the floor of the compartment, defined by the front face of the front piston, the medicament is fed out of the tube end. When dealing with a liquid, as when the apparatus is filling the rear compartment with solvent, it is standard to withdraw the filling tube upward as the liquid level rises in order to avoid turbulence.

In each of these operations it is essential that the syringe body be oriented accurately with respect to the setting or filling tube. Since, however, the syringe bodies are often formed of glass, they are gripped in holders with cushioned jaws so that the orientation of their axes cannot be guaranteed to lie on the center axis of the filling or setting tube. The result can be broken or scratched syringe bodies.

OBJECTS OF THE INVENTION

It is therefore an object of the present invention to provide an improved apparatus for setting an object—a piston or a fluid—into a syringe body.

Another object is the provision of such an improved apparatus for setting an object—a piston or a fluid—into a syringe body which overcomes the above-given disadvantages, that is which inserts the tube into the syringe body exactly on the axis of the syringe body.

SUMMARY OF THE INVENTION

An object, e.g. a piston or a fluid medicament, is inserted into a tubular syringe body centered on a syringe axis and having a pair of ends by an apparatus having according to the invention a support movable axially forward toward and axially rearward away from the body and a tube extending along a sleeve axis generally parallel to the syringe axis, having a rear end fixed in the support and a front end fittable inside the syringe. A centering sleeve is formed centered on the sleeve axis with a generally frustoconical centering surface engageable with the rear body end surrounding the setting tube. This sleeve is displaceable axially on the support between a front position with the centering surface projecting axially forward past the tube front end and a rear position with the tube front end projecting axially forward past the centering surface. The support is displaced axially forward toward the body and thereby engages the centering surface coaxially with the body rear end. Thereafter the setting tube is pressed coaxially through the centering sleeve into the syringe body.

With this system, therefore, the centering sleeve serves for transversely displacing the front end of the setting tube and/or the rear end of the syringe body so that the syringe axis and the tube axis are perfectly aligned before the tube is actually inserted into it. Even if the syringe is not perfectly aligned with the setting tube, by the time the setting tube is advanced enough to poke into the rear syringe end, the two elements will be perfectly coaxial.

The centering surface can be axially flared toward the syringe body. Alternately it is axially tapered toward the syringe body. In the latter case the centering sleeve can be formed with a downwardly flared centering skirt centered on the tube axis and axially level with the centering surface. The taper of this skirt, which is normally of highly flexible material, is such that it engages the syringe rear end before the centering surface, something that is particularly useful with a syringe having a rolled rear-end rim since it allows the centering surface to be of downwardly tapering shape.

According to the invention a spring braced between the support and the centering sleeve urges the sleeve into the front position. The tube is normally somewhat elastically flexible so that its lower front end is somewhat transversely displaceable relative to the axes. The sleeve's front end can similarly move transversely so that when it fits with the syringe rear end, which can be offset transversely, it will move sideways and move the tube over too for perfect coaxial alignment.

The support in accordance with the invention is provided with a mounting sleeve generally centered on the tube axis and slidably surrounding the centering sleeve. Furthermore the centering sleeve and mounting sleeve define an axially extending space opening at the centering surface. The apparatus further has according to the invention means for aspirating gas in through the space. Thus any particles or droplets that might be generated by the filling operation will be aspirated right at the syringe rear end. To aid this aspiration one of the sleeves is formed with an axially extending and radially open groove extending a full length of the space and the centering surface is formed to seal tightly with the rear syringe end.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
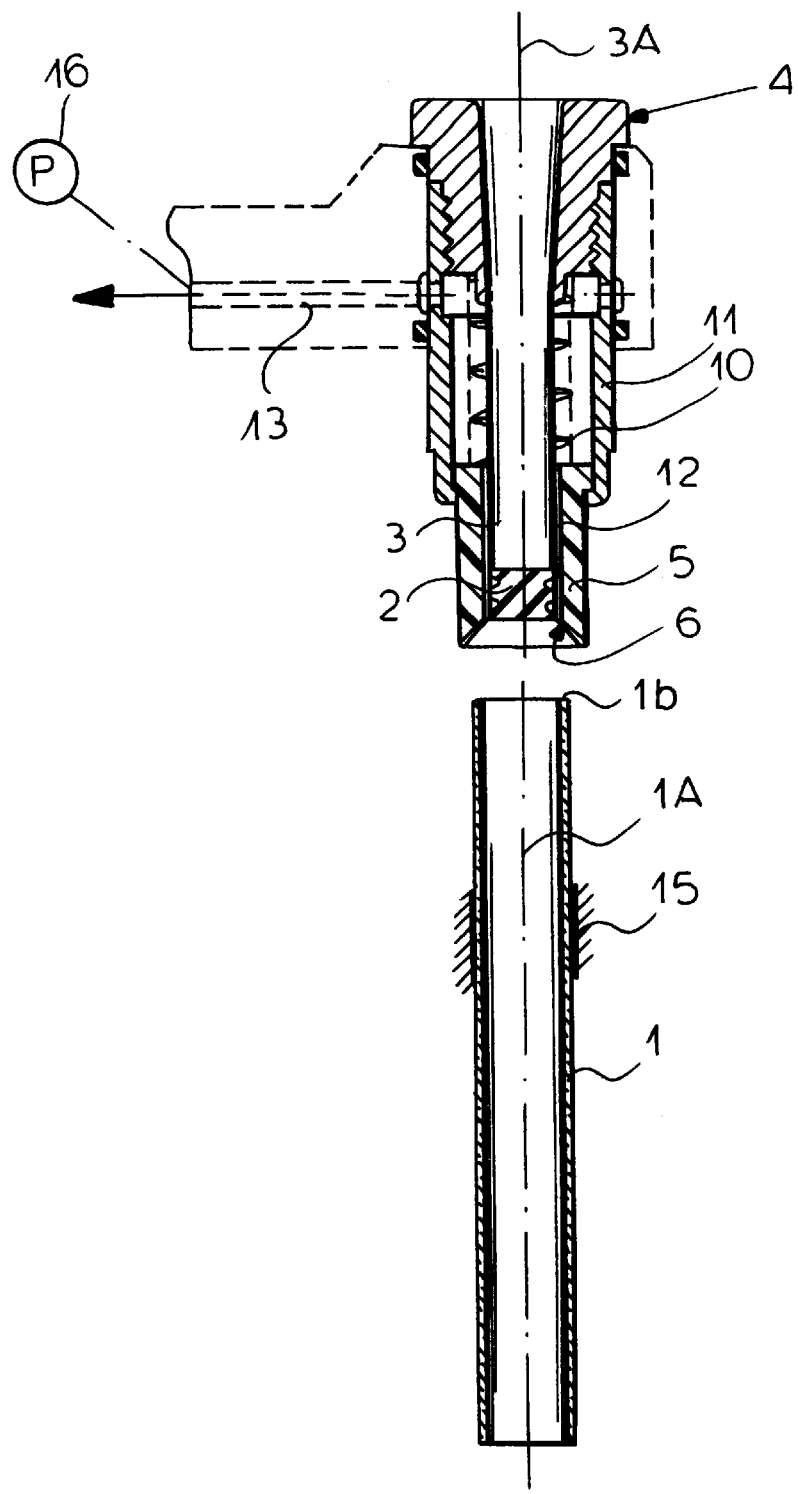
FIG. 1 is a large-scale vertical section through a piston-setting apparatus according to the invention.

As seen in the drawing a glass tubular syringe body 1 is centered on an axis 1A and has a small-diameter front end 1a set for a Luer or other connection, a large-diameter rear end 1b which may be formed with an outwardly projecting finger-grip rim 8, and a central bypass passage 1c. A piston 2 formed as a cylindrical elastomeric plug normally subdivides the interior of the syringe body 1 into a front compartment adapted to receive a fluid—liquid or powder—medicament and a rear compartment adapted to receive a liquid solvent.

FIGS. 1 through 7 show devices for setting the piston 2 at the desired location inside the body 1. This apparatus comprises a clamp shown schematically at 15 which orients the body 1 with its axis 1A vertical and a thin-walled setting tube 3 extending along an axis 3A and having an upper end fixed in a holder 4 and a lower end holding the piston 2. An outside diameter of this setting tube 3 is slightly less than an inside diameter of the body 1. The holder 4 further carries a mounting sleeve 11 in whose lower end is mounted a centering sleeve 5 that surrounds the lower end of the tube 3 with slight play indicated at space 12. This centering sleeve 5 is biased downward by a spring 10 raced against the holder 4 and can tip so that the axis 3A is somewhat movable relative to the holder 4.

Figure 3:
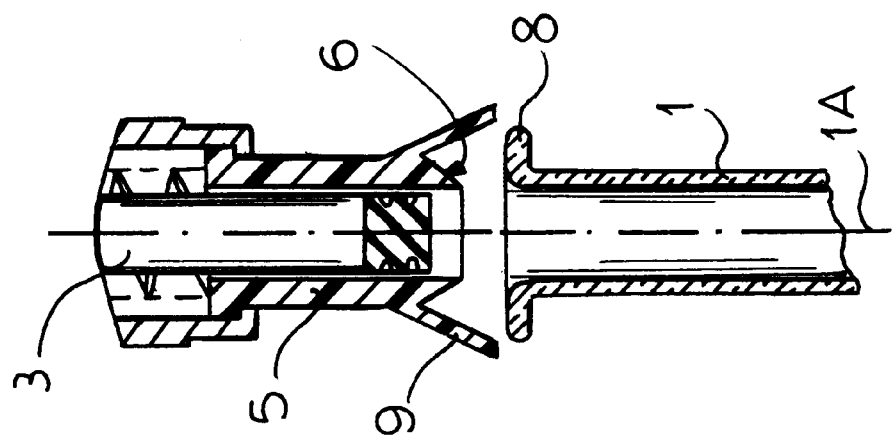
FIGS. 2 and 3 are views like FIG. 1 showing two further piston-setting apparatuses.
Figure 2:
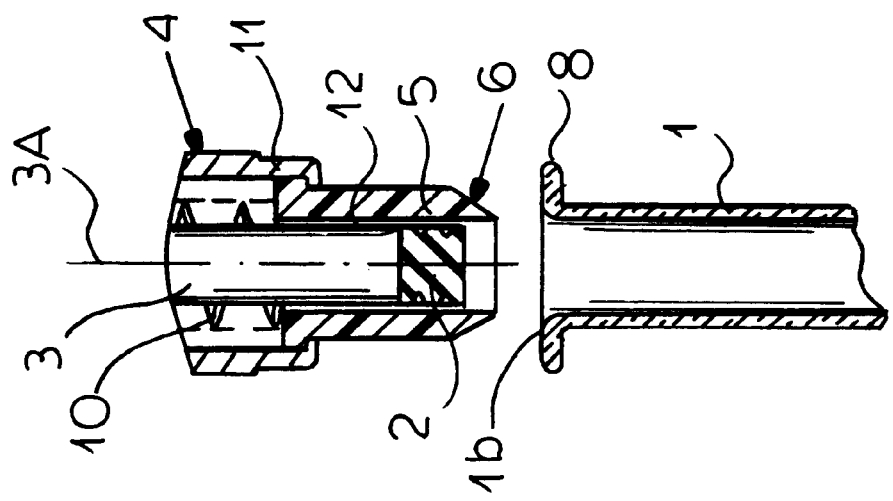

The lower end of the centering sleeve 5 is formed centered on the axis 3A with a frustoconical centering surface 6. In FIG. 1 this surface flares downward and is of an outside diameter that is substantially greater than an outside diameter of the tubular body 1. In FIG. 2 it tapers downward and has an inside diameter that is slightly less than an inside diameter of the body 1, as here the body 1 has a radially projecting finger-grip rim 8. FIG. 3 shows a further arrangement where the surface 6 is downwardly tapered as in FIG. 2, but the centering sleeve 5 is provided with a downwardly flared frustoconical skirt 9 whose outside diameter is greater even than the outside diameter of the rim 8.

Figure 5:
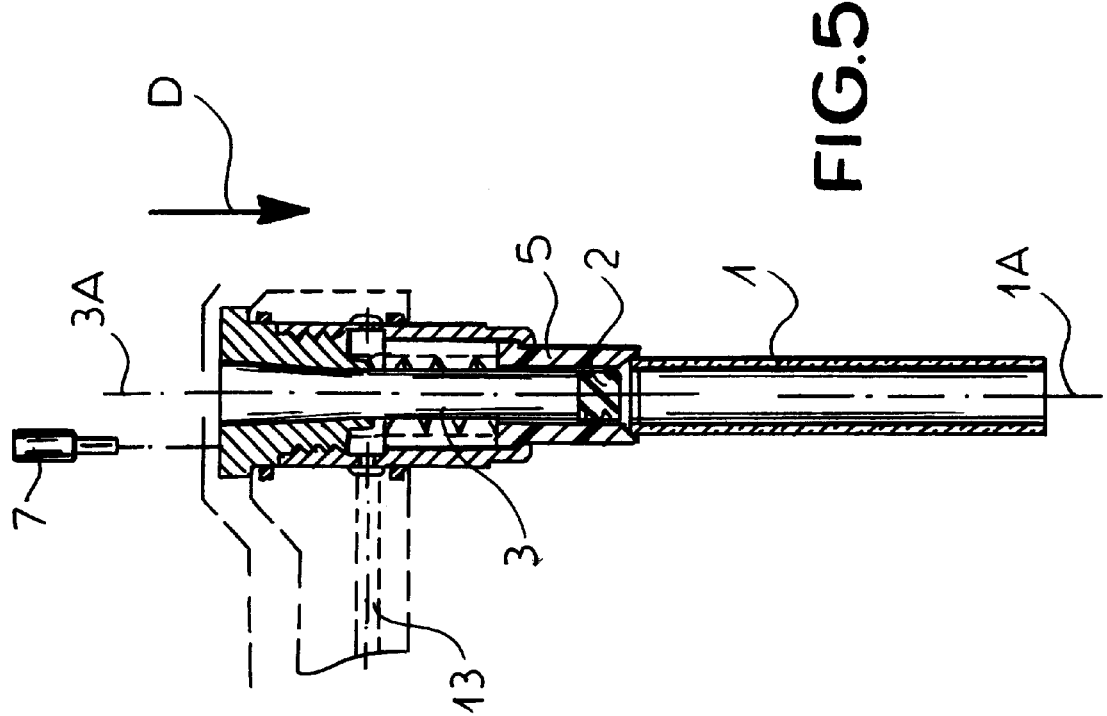
FIGS. 4 and 5 show the apparatuses of FIGS. 1 and 2 in a starting position engaging the syringe body.
Figure 4:
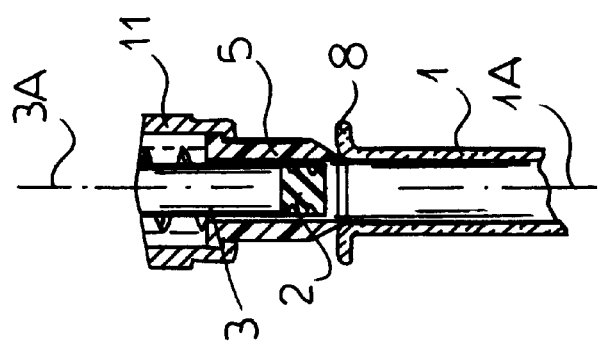
Figure 7:
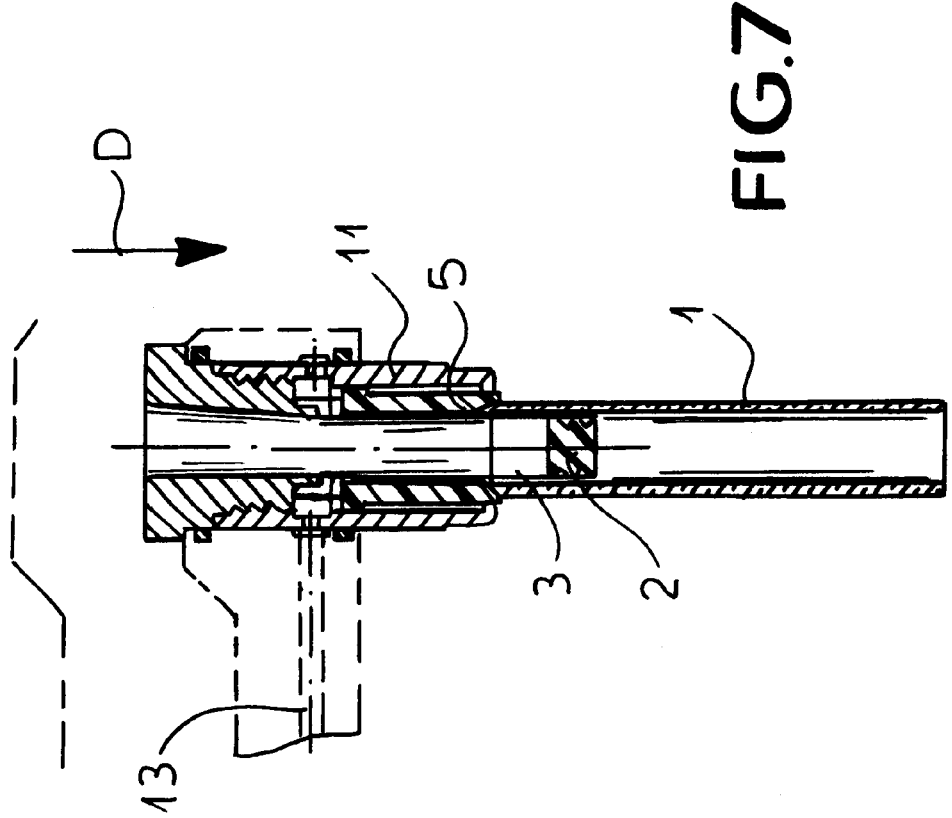
FIGS. 6 and 7 show the apparatuses of FIGS. 1 and 2 with the piston inserted into the syringe body.
Figure 6:
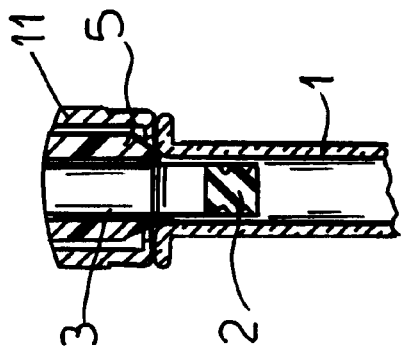

In use as shown in FIGS. 4 and 5 the holder 4 is first lowered by an actuator shown schematically at 7 until the surface 6 just barely settles on or in the rear end 1b of the body 1. This action shifts the axis 3A so as to align it perfectly with the axis 1A, although there might instead or in addition be lateral deflection of the axis 1A to align it with the axis 3A. Further downward shifting of the holder 4 will cause the sleeve 5 to shift upward against the force of the spring 10 in the sleeve 11 while pushing the setting tube 3 coaxially down in the syringe body 1. Once the desired position just rearward of the bypass 1c is reached, the piston 2 is moved forward out of the end of the tube 3, whereupon it expands radially and assumes its starting position in the body 1.

The space 12 is connected to a suction passage 13 in turn connected to a pump 16. The surface 6 is of a somewhat soft sealing material so that the pump 16 can create a subatmospheric pressure in the syringe body 1 (presuming its front end 1a is plugged) which can be used to suck the piston 2 forward out of the end of the tube 3.

Figure 8:
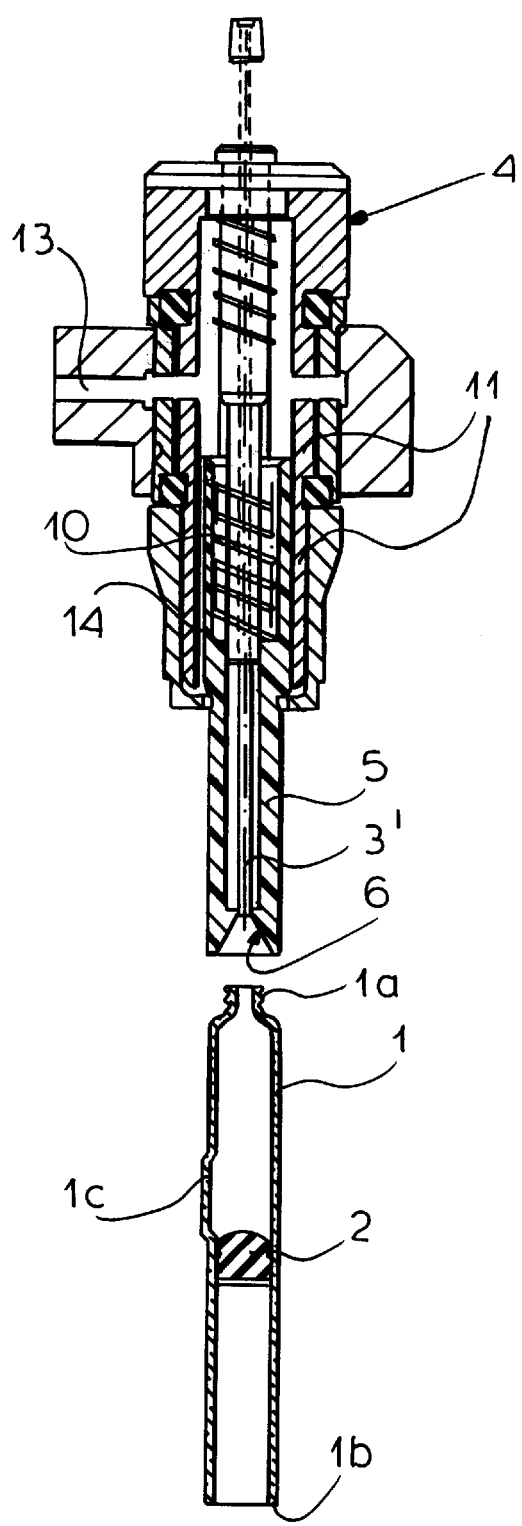
FIGS. 8 and 9 show a fluid-filling apparatus at two stages of a filling operation.
Figure 9:
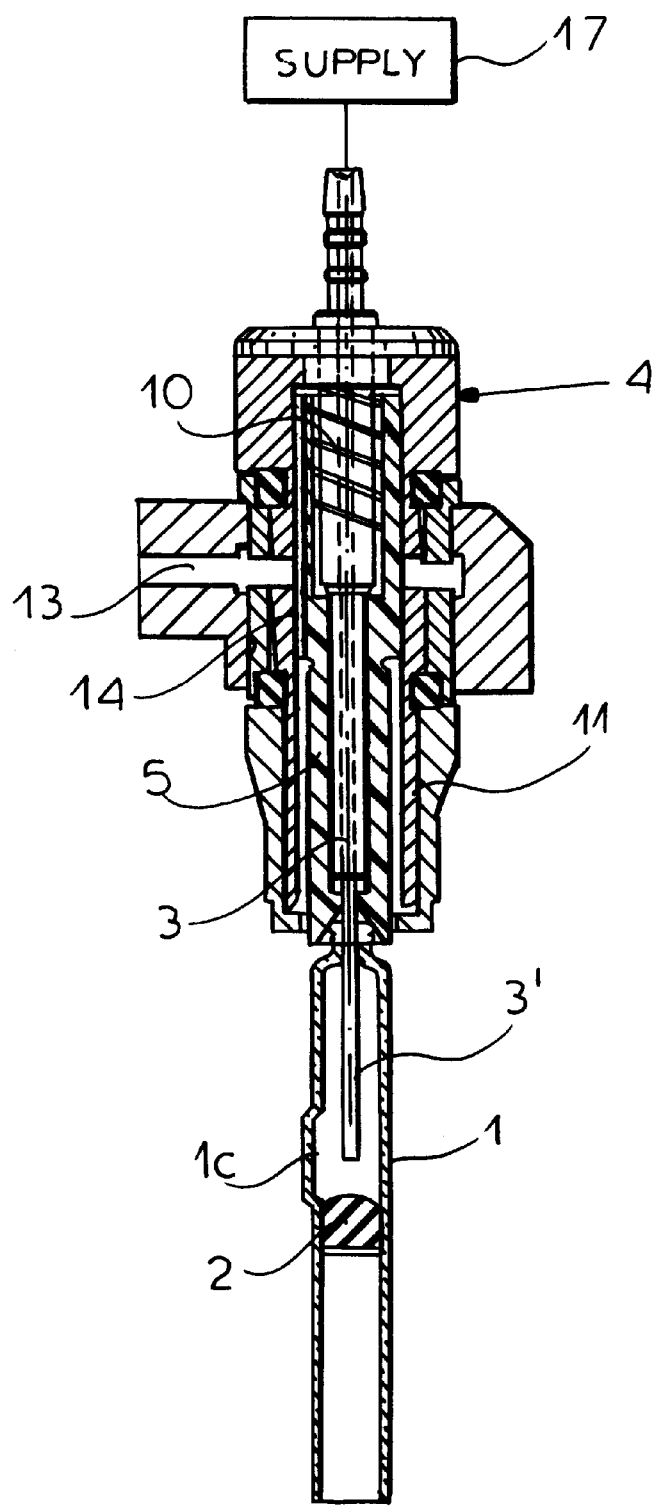

In FIGS. 8 and 9 the tube 3' is formed as a small-diameter lance whose rear end is connected to a supply 17 of a fluent medicament. Here the centering sleeve 5 is fitted to the front end 1a and the tube 3' is extended down into the front compartment, whereupon the supply 17 injects the medicament into the body 1. During this operation any droplets or particles are aspirated through the space 12 and passage 13. In addition the sleeve 5 is formed with an axially outwardly open groove 14 to augment such aspiration.

We claim:

1. An apparatus for inserting an object into a tubular syringe body centered on a syringe axis and having a pair of ends, the apparatus comprising:

a support movable axially forward toward and axially rearward away from the body;

a tube extending along a tube axis generally parallel to the syringe axis, having a rear end fixed in the support and a front end fittable inside the syringe;

a centering sleeve formed centered on the tube axis with a generally frustoconical centering surface engageable with the rear body end surrounding the tube, the sleeve being displaceable axially on the support between a front position with the centering surface projecting axially forward past the tube front end and a rear position with the tube front end projecting axially forward past the centering surface; and means for displacing the support axially forward toward the body and thereby engaging the centering surface coaxially with the body rear end and thereafter pressing the tube coaxially through the centering sleeve into the syringe body.

2. The apparatus defined in claim 1 wherein the centering surface is axially flared toward the syringe body.

3. The apparatus defined in claim 1 wherein the centering surface is axially tapered toward the syringe body.

4. The apparatus defined in claim 3 wherein the centering sleeve is formed with a downwardly flared centering skirt centered on the tube axis and axially level with the centering surface.

5. The apparatus defined in claim 1, further comprising
   means including a spring braced between the support and the centering sleeve for urging the sleeve into the front position.

6. The apparatus defined in claim 1 wherein the support is provided with a mounting sleeve generally centered on the tube axis and slidably surrounding the centering sleeve.

7. The apparatus defined in claim 6 wherein the centering sleeve and mounting sleeve define an axially extending space opening at the centering surface, the apparatus further comprising
   means for aspirating gas in through the space.

8. The apparatus defined in claim 7, wherein one of the sleeves is formed with an axially extending and radially open groove extending a full length of the space.

9. The apparatus defined in claim 6 wherein the centering surface is formed to seal tightly with the rear syringe end.

* * * * *